United States Patent [19]

Lowther et al.

[11] Patent Number: 4,575,383

[45] Date of Patent: Mar. 11, 1986

[54] PROCESS FOR PRODUCING ACETYLENE USING A HETEROGENEOUS MIXTURE

[75] Inventors: Frank E. Lowther, Chatsworth, Calif.; Frederick L. Voelz, Munster, Ind.

[73] Assignee: Atlantic Richfield Company, Los Angeles, Calif.

[21] Appl. No.: 602,320

[22] Filed: Apr. 20, 1984

[51] Int. Cl.[4] ............................................. C07C 2/78
[52] U.S. Cl. ........................... 48/212; 48/196 R; 48/DIG. 8; 123/1 R; 423/458; 423/650; 585/540
[58] Field of Search ............... 585/540; 48/212, 213, 48/214 R, DIG. 8, 196 R; 423/650, 458; 123/1 R

[56] References Cited

U.S. PATENT DOCUMENTS

| | | | |
|---|---|---|---|
| 2,484,249 | 10/1949 | Ruble | 48/196 R |
| 2,727,933 | 12/1955 | Evans et al. | 585/540 |
| 2,748,179 | 5/1956 | Retailliau | 48/196 R |
| 2,823,243 | 2/1958 | Robinson | 48/196 R |
| 2,914,041 | 11/1959 | Froehlich | 123/1 R |

Primary Examiner—Jay H. Woo
Assistant Examiner—Joye L. Woodard
Attorney, Agent, or Firm—Craig E. Larson

[57] ABSTRACT

A method for converting methane to acetylene is disclosed wherein a hydrocarbon fuel is compressed, an oxygen-containing gas is introduced into a portion of the compressed hydrocarbon fuel and ignited to produce heat which causes the remaining portion of the hydrocarbon fuel to react to form a product gas containing acetylene.

19 Claims, 1 Drawing Figure

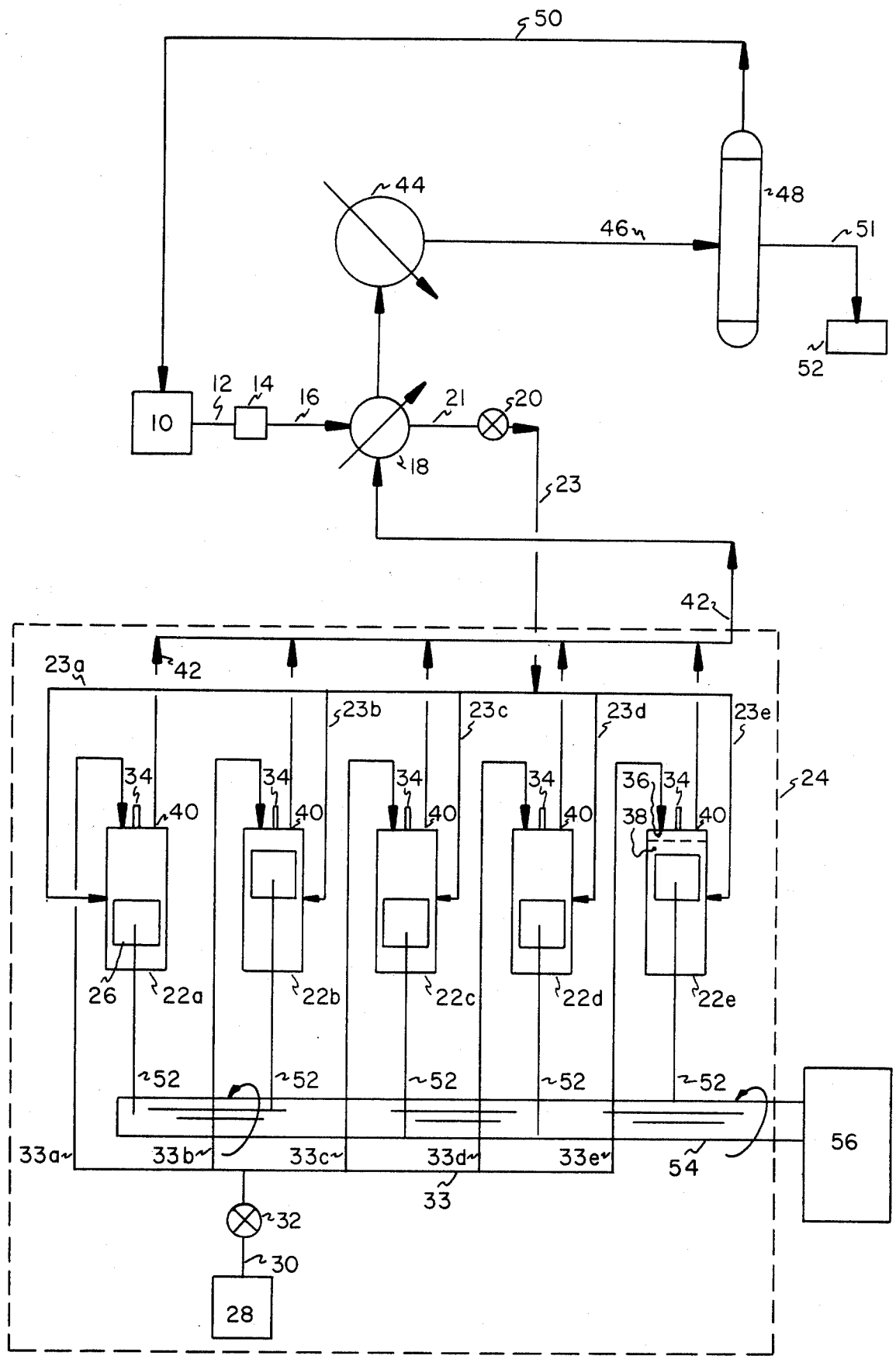

PROCESS FOR PRODUCING ACETYLENE USING A HETEROGENEOUS MIXTURE

BACKGROUND OF THE INVENTION

1. Field of the Invention

The present invention relates to the thermal conversion of methane to acetylene and particularly relates to compression, rapid heating, injection of oxygen, and decompression, and short residence time reaction of methane to produce acetylene in the combustion space of a cyclically operated internal combustion engine.

2. Setting of the Invention

It is known that hydrocarbons, including methane, as well as higher aliphatic and cyclic hydrocarbons, will yield acetylene and ethylene when subjected to partial combustion or thermal cracking processes. In thermal cracking processes, the necessary heat for the reaction is supplied to the hydrocarbon charge by external or indirect heating. Thermal cracking has not been found to be commercially viable for methane pyrolysis. In partial combustion processes, necessary heat for the reaction is supplied by combusting part of the methane charge. The principal difficulty with the partial combustion system is coke formation within the reaction system. Both processes require high temperatures to form acetylene, together with rapid cooling of the reaction product to avoid decomposition of the acetylene formed.

DESCRIPTION OF THE PERTINENT ART

Pertinent art includes U.S. Pat. No. 1,939,018 (+018), which discloses a method of combusting a fuel such as gasoline, natural gas and other hydrocarbons to form product gases such as aldehydes, alcohols and other oxygenated products in an internal combustion engine, including the steps of admitting the fuel and an insufficient amount of an oxidizing agent into the combustion chamber of the engine, igniting the mixture, causing combustion to occur in the chamber, removing the exhaust gases from the chamber and immediately cooling the exhaust gases, and recovering the product gases from the exhaust gases. U.S. Pat. No. 1,939,018 recognizes that the compression of the fuel/oxidizing agent mixture relates directly to the temperature of the mixture before and after combustion. In order to control temperature, a diluent gas such as nitrogen or water vapor is admitted with the fuel/oxidizing agent mixture to the combustion chamber.

In addition, to achieve greater product yield, a catalyst such as nitrogen dioxide, nitric acid or a finely divided metal oxide was disclosed as an addition to the fuel/oxidizing agent mixture prior to ignition.

The method of '018 produces oxygenated products in relation to the amount of power produced. The method details also using two sets of chambers within the same engine for production of maximum power from the first set and a maximum product under a controlled lower temperature in the second set.

Also included in pertinent art is U.S. Pat. No. 2,748,179 ('179), which dicloses another method for conversion of low molecular weight hydrocarbons to olefins and aromatics, including the steps of preheating to 200° to 400° F. a mixture of hydrocarbons and an oxygen-containing gas having 0.5 to 2.8 moles of free oxygen per mole of hydrocarbon, admitting the mixture to an externally unheated reaction zone, compressing the mixture in the zone to about 1/10 to 1/20 of the original volume of the zone about 100 to 450 times a minute so that the temperature is increased substantially to a level conducive to a limited reaction between the hydrocarbons and the free oxygen, rapidly expanding the reaction products to reduce the temperature and withdrawing the reaction products from the zone. The fuel/oxygen-containing gas mixture may be diluted with an inert gas such as steam or nitrogen. The fuels disclosed as being useful in the method of '179 include gaseous and liquid paraffinic hydrocarbons and liquid napthenic hydrocarbons. The method is disclosed as being particularly useful on normally low molecular weight liquid hydrocarbons such as n-pentane and n-hexane.

Pertinent art also includes an article entitled "The Production of Synthesis Gas and Power in a Compression IgnitionEngine" authored by G. A. Karim and N. P. W. Moore. In this article, a method for producing a synthesis gas using a single-carrier, compression-ignition, four-stroke engine of an open chamber type was disclosed. The natural gas and air were introduced into the chamber, compressed to a ratio of 14.2:1, and ignited by injection of a small quantity of liquid fuel such as diesel fuel near the top dead center (T.D.C.) position in the cycle of the engine piston. The liquid fuel used was usually less than 10 percent of the total full load quantity. The authors noted that two stages took place during the synthesis gas production. The first stage was the consumption of most of the oxygen following the ignition of the liquid fuel to produce carbon dioxide and water and the release of the energy which raises the temperature level of the mixture held in the compression chamber. When the higher temperature level was obtained throughout the combustion chamber, a second step included the reforming reactions of the feed gas which proceeded at a substantial rate and produced synthesis gas. During expansion, these reactions ceased as a certain reduced temperature level was attained. Rapid quenching rates were provided by high-speed engines resulting in better gas yields and the possible production of other compounds such as acetylene. However, in all testing, Karim and Moore found that acetylene was absent from the exhaust gas produced during the experiments. It was stated that the methane was converted to acetylene in the flame front very rapidly, but to an extent far short of equilibrium. The acetylene would subsequently react with methane and water to produce hydrogen and carbon monoxide.

Further pertinent art includes U.S. Pat. No. 2,823,243 ('243), which discloses a method of pyrolysis of hydrocarbons to produce an acetylene-containing product. The method includes the steps of burning hydrogen and oxygen to form a combustion gas having a temperature of between 4500° and 5300° F.; introducing a stream of gas (hydrogen or steam) to reduce the temperature of the combustion gas to not higher than 4200° F.; preheating a methane-containing gas to 1800° to 2400° F.; introducing the heated gas into the combustion gas to produce a gas admixture having a temperature between 2400° and 3500° F.; increasing the linear velocity of the resulting mixture to 200 to 500 feet per second; decreasing the velocity; maintaining the mixture in reaction for a time between 0.001 and 0.05 seconds; quenching the mixture to below pyrolysis temperature; and recovering the pyrolysis products.

The principal object of the present invention is to provide the process of production of acetylene and ethylene from methane. A more specific object of the present invention is to maximize the acetylene yields by minimizing feed hydrocarbon losses to carbon dioxide and coke. A further object is to maximize the overall yield of acetylene from a methane feedstock while still producing usable power. A still additional object of the present invention is to provide a convenient small-scale method of converting a methane-containing natural gas to power and acetylene which can be further converted into a liquid form for transport.

SUMMARY OF THE INVENTION

The present invention covers a process for converting low molecular weight normally gaseous hydrocarbons into valuable hydrocarbons containing acetylene and $C_2+$ hydrocarbons and includes the steps of introducing the gaseous hydrocarbons into a reaction zone, compressing the gaseous hydrocarbons in the zone to about 1/5 to about 1/13 of the original volume of the reaction zone, introducing an oxygen-containing gas into a portion of the compressed hydrocarbons in the reaction zone, the mole ratio of hydrocarbons to oxygen ranging from about 0.75:1 to about 2:1, igniting the mixture causing combustion of a portion of the hydrocarbons and the release of heat energy into the remaining portion of the hydrocarbons so that the temperature of the remaining portion is increased substantially to a level conducive to a limited reaction under compression to produce an acetylene-containing reaction product, rapidly thereafter expanding the reaction product to reduce the temperature of the reaction product, removing the reaction product from the reaction zone and cooling the removed reaction product. These steps are repeated about 500 and about 2000 times per minute.

BRIEF DESCRIPTION OF THE DRAWINGS

The FIGURE is a schematic representation of an apparatus used in the process of the present invention.

DETAILED DESCRIPTION OF THE INVENTION

The process of the present invention may best be illustrated in accordance with the FIGURE, which shows one embodiment of the present invention. For purposes of the explanation of this embodiment, methane is employed, although it will be understood that other hydrocarbons such as natural gas may be and are used. The term "methane" is used in the description of the embodiment, but should not be read to limit the type of hydrocarbon useful in this process. The hydrocarbons used in the process of the present invention may be any gaseous, low molecular weight hydrocarbon which is combustible such as city gas, natural gas, ethane, propane, butane, pentane, and other gaseous petroleum products. The feedstock useful in the present invention also includes hydrocarbons which can be vaporized at conditions under which the process is conducted. The hydrocarbons may include additional hydrogen. Further, hydrogen or other combustible materials may be introduced into a primary zone to be mixed with the oxygen.

The methane is pumped from storage tank 10 through line 12 to metering device 14 and thence through line 16 to heat exchanger 18, where it is heated to a desired temperature. The methane flows from heat exchanger 18 via line 21 and is regulated by means of valve 20 into line 21 leading from heat exchanger 18 into main line 23, then into lines 23a, b, c, d, and e, and finally into reaction zones 22a, b, c, d, and e. Reaction zones 22 are a battery of internal combustion cylinders as part of a multicylinder internal combustion engine 24. Pistons 26 of engine 24 are externally actuated to alternately compress and expand the methane and the reaction product.

A predetermined amount of methane is metered into reaction zones 22. Pistons 26 move within reaction zones 22 to compress the methane held in reaction zones 22. During the compression stroke, an amount of oxygen-containing gas is introduced from oxygen source 28 via line 30 and controlled by valve 32 into line 33, which leads into reaction zones 22.

Referring to reaction zones 22, the oxygen-containing gas in intermixed with a portion 36 of the compressed methane. At a second predetermined pressure, also near the top of the compression stroke, a spark is provided by means 34 to ignite the mixture of the oxygen-containing gas and portion 36 of the compressed methane. This ignition causes combustion of the mixture of oxygen-containing gas and methane, which in turn raises the temperature of both the combustion gases and the remaining unmixed portion 38 of the compressed methane. Portion 38 of the compressed methane contains only a minor portion of free oxygen. Following the combustion and the reaction, pistons 26 move within reaction zones 22 to expand the combustion gases and the reaction gases. The gaseous mixture of combustion and reaction is partially cooled during the expansion stroke of pistons 26.

Power is generated by the expansion of the hot gases contained in reaction zones 22 against pistons 26, which in turn drive piston rods 52 downward during various stages of the overall process. The movement of piston rods 52 in turn drives shaft 54. Shaft 54 is connected to a power collection means 56 for generation of useful mechanical power or conversion to electrical power.

The gases are withdrawn via outlets 40 as pistons 26 reach full expansion and during a portion of the exhaust stroke. From outlets 40, the hot product gases flow to heat exchanger 18 through lines 42 to be cooled by incoming methane stream 16. The cooled gases from heat exchanger 18 are moved to condenser 44 via line 45 to be cooled further to a desired temperature. The cooled gases are moved via line 46 to separation tower 48. The cooled gases may be separated and purified in separation tower 48 by any of the various known techniques for recovery of individual products such as by distillation, absorption, gravity separation and the like. Products, including acetylene, as well as recoverable olefins such as ethylene, are recovered via line 51 in product tank 52. Unused methane can be recycled via line 50 to methane source 10.

The oxygen-containing gas may be air, air enriched with oxygen, oxygen, mixtures of them or compounds containing one or more of them which support combustion; that is, compounds that will react with and oxidize the hydrocarbon fuel under conditions of combustion in an internal combustion engine. Preferably, the oxygen-containing gas is either air or oxygen. More preferably, it is oxygen. Still more preferably, the oxygen has a purity greater than 99.5 percent.

An important feature of the present invention is the rapid formation of a heat source within the reaction zone without the combustion of the entire hydrocarbon fuel held within the reaction zone. Thus, the oxygen that is introduced into the reaction zone is either reacted with a stoichiometric amount of the hydrocarbons held within a portion of the reaction zone or does not contact the remaining portion of the hydrocarbons. This minimization of contact of unreacted oxygen with reactant radicals in the main portion of the oxygen-free compressed methane in turn minimizes methane combustion and consequent coke loss in the process. The heat generated by combustion raises the temperature of the remaining portion of the hydrocarbon fuel to a temperature at which the methane is converted to form a desirable reaction product containing acetylene and $C_2+$ hydrocarbons.

The reaction within the engine is sensitive to temperature, time, compression ratio, expansion ratio, degree of mixing of the oxygen-containing gas with the hydrocarbon fuel, engine design, ratio of hydrocarbons to oxygen, and ratio of combusted hydrocarbons to total compressed hydrocarbons. Relatively long contact time due to low revolutions per minute (rpm) of the internal combustion engine produces carbon dioxide and water, rather than the desired product gas. A high preheat temperature (for instance, about 400° F.) causes prereaction of the mixture, which has the effect of reducing the amount of desired acetylene and $C_2+$ hydrocarbons in the reaction product.

The mole ratio of methane to oxygen should range from about 0.75:1 to about 2:1. Preferably, the mole ratio of methane to oxygen is between about 1.2:1 to about 1.3:1. The mole ratio is selected to cause a predetermined spike temperature after ignition. The mole ratio is calculated based upon the entire quantity of hydrocarbons contained in the reaction zone, even though only a portion of it is combusted. Preferably, the mole ratio of methane to oxygen is between about 1.1:1 to about 1.7:1.

The number of compressions per minute may vary from about 500 to about 2000 times per minute. Preferably, the compressions occur about 800 to about 1400 times per minute. More preferably, the compressions occur about 1000 to about 1200 times per minute.

The timing of ignition is set such that shaft 54 is continuously turned at a smooth rate. Preferably, the timing is set to be between about 20° before T.D.C. and about 10° after T.D.C. More preferably, the timing is about T.D.C. to about 10° after T.D.C.

Preferably, a mixture of hydrogen and oxygen is injected into the primary zone of compressed methane and ignited. Preferably, the injection is made into a secondary zone in communication with the primary zone. The oxygen and hydrogen are introduced into the secondary zone in an amount to provide a mole ratio of hydrogen to oxygen within the range of about 1.95:1 to about 2.2:1. This ratio is dependent upon the design of the engine.

The compression ratio ranges from about 5:1 to about 16:1, and preferably from about 8:1 to about 14:1. Most preferably, the ratio is about 12:1. The temperature obtained at T.D.C. should range from about 2700° to about 2900° F. The temperature obtained at T.D.C. may be controlled by compressing the methane to a higher ratio, preheating the methane before compression, or a combination thereof.

The expansion rate should be as rapid as possible and need not be identical to the compression rate. The methane may be injected under a vacuum or after partial completion of the piston cycle. Preferably, however, the reaction product gases are expanded into a large volume outside the reaction zone to increase the expansion rate. Preferably, the expansion ratio should be from about 10:1 to about 20:1. More preferably, the expansion ratio is about 13:1 to about 18:1.

If a lubricant is used with the piston and cylinder, it is preferable that the lubricant be convertible to a usable product.

It is preferable to cool the exhaust gases immediately after reaction or at least as they are discharged from outlets 40 of the engine for purposes of preventing the destruction of unstable compounds. It is more preferable to introduce to reaction zones 22 cooling quench gas during the expansion step of pistons 26 to quickly lower the temperature of the product gases. The cooling quench gas may be water, steam, water vapor, methane, ethane, propane, butane, or other fluid which can be readily separated from the product gases in separation tower 48. Alternatively, or in combination with cooling, the reaction gas is contacted with a catalyst upon exiting outlets 40 or following cooling to convert more methane to the desired end products.

Alternatively, a secondary zone, not shown, in communication with reaction zones 22 when pistons 26 are at the top of the compression stroke, may be provided. The oxygen is introduced and ignited with timing similar to the primary zone. Methane is metered into reaction zones 22 and the secondary zone and compressed by pistons 26. The oxygen is injected into the secondary zone mixed with the methane contained therein, and the mixture is ignited to release heat to reaction zones 22 and increase the temperature of the compressed methane to a reaction temperature. Pistons 26 move downward in reaction zones 22 to expand the reaction products and cool them as described above.

Preferably, a combustible fuel such as hydrogen is premixed with the oxygen and injected into the secondary zone and ignited. The combustible fuel used in the secondary zone need not be methane or the same as the gaseous hydrocarbons used in reaction zones 22. Preferably, the combustible fuel is hydrogen, which is a by-product of the process of the present invention.

The matter of generating power efficiently is typically secondary to production of a maximum amount of desired end products; that is, acetylene. Conditions may be adjusted with use-either a different natural gas or a different oxidizing agent such as air or pure oxygen or air enriched with oxygen. The maximum amount of power is not always obtained simultaneously with the maximum yield of incompletely oxidized desired end products.

Alternatively, a number of the cylinders may be fed with power producing fuel oxygen ratios so as to drive the shaft and the other cylinders which would be directed to maximum methane conversion.

The oxygen-containing gas or the oxygen-containing gas/hydrogen mixture should be introduced into reaction zones 22 in such a manner as to minimize the mixing of such gases with more of the compressed hydrocarbons in the reaction zone than necessary for the combustion of the hydrocarbons and the gas. A preferred method of introduction is tangentially in the same direction as the swirl caused within the reaction zone by compression.

EXAMPLE

A series of tests using a spark-ignited, single-cylinder, four-cycle, internal combustion engine to demonstrate the effect of engine speed, compression ratio, ignition spark timing, and methane feedrate and oxygen injector pressure on the conversion of methane to $C_2+$ hydrocarbons was conducted. The engine speed was set at 700 rpm and a compression ratio of 10:1. The ignition and injector timings were set at 20° and 45° before T.D.C. and closed prior to the spark plug firing. Methane was aspirated into the engine chamber by the engine while a 50/50 mixture of oxygen and nitrogen was injected. The flow rate of the methane was maintained at about 4.75 ft.$^3$/min. and 3.95 ft.$^3$/min. The pressure of the oxygen/nitrogen injector was set at 300 and 500 psig. The engine air intake system was closed, therefore the only source of oxygen was through the injector. For each set of conditions, the aspirated volume of methane was held constant and the injected volume was changed by adjusting the inlet pressure to the solenoid valve. In all cases, the injector was not activated until the desired flow of methane was achieved. At that time, the ignition system was turned on and the injector activated at a low inlet pressure. The inlet pressure was then increased until the engine was running. Since the volume of gas injected could not be readily measured directly, exhaust gas samples were obtained at the test condition with and without the ignition system activated. With the ignition system off and the exhaust gas temperature equilibrated, the composition of the exhaust gas was essentially the same as the intake mixture. With the ignition off in Examples 1 and 2, 1.2 horsepower was required to motor the engine at the test speed. This power is required to compress the aspirated and injected gases and overcome the friction in the engine. The exhaust gas and injector temperatures are relatively low during the motored operation. Operation of the engine with the ignition on (spark plug firing) shows the load to be zero. This means that the engine is producing sufficient power to compress the intake/injected gases and overcome friction (i.e., power is being produced). The exhaust gas was analyzed with a gas chromatograph.

TABLE 1

| EX | RPM | COM-PRES-SION RATIO | IGNITION SPARK TIMING | RATIO OF METHANE TO OXYGEN | $C_2$ (%) |
|---|---|---|---|---|---|
| 1 | 700 | 10:1 | None | 1:1 | 0.0 |
| 2 | 700 | 10:1 | None | 1:1 | 0.0 |
| 3 | 700 | 10:1 | 20° BTDC | 1:1 | 0.3 |
| 4 | 700 | 10:1 | 20° BTDC | 1:1 | 0.4 |

The maximum conversion to $C_2+$ hydrocarbons from methane occurred when the engine was operated at 700 rpm with a compression ratio of 10:1, spark timing at 20° before T.D.C., a methane injection rate of 4.75 ft.$^3$/min., and an injector pressure of 300 psig. However, ignition timing after T.D.C. is recommended to maximize the chemical products rather than the mechanical power. Under these conditions, approximately 0.3 percent of the methane on a carbon basis was converted to acetylene and 0.3 percent was converted to ethylene. Approximately 50 percent of the methane was converted to a reaction product. The exhaust gas temperature reached a maximum value of 725° F. and the engine operated without external power. Increasing the concentration of the methane and oxygen reduced the conversion rate to acetylene and ethylene.

The versatility of the present invention is well demonstrated in that desired compounds are produced which can be transported or converted to highly valued hydrocarbons and that mechanical and/or electrical power is also produced.

The invention which is claimed is:

1. A process for converting low molecular weight hydrocarbons to acetylene which comprises the steps of:
   introducing said hydrocarbons into a first reaction zone;
   compressing said hydrocarbons in said first reaction zone to a volume which ranges from about 1/5 to about 1/10 of the original volume of said hydrocarbons in said first reaction zone;
   introducing an oxygen-containing gas into said first reaction zone to intermix with a portion of said compressed hydrocarbons, the mole ratio of said hydrocarbons to said oxygen-containing gas comprising between 0.75:1 to about 2:1;
   igniting said mixture causing partial combustion of said portion of said hydrocarbons and the release of heat energy so that the temperature of the remaining portion of said hydrocarbons is increased substantially to a level conducive to a limited reaction under compression to produce an acetylene-containing reaction product;
   expanding said reaction product to reduce the temperature of said reaction product;
   recovering power from said expanding step;
   removing said reaction product from said first reaction zone; and
   cooling said product; said steps are repeated from about 500 to about 2000 times per minute.

2. The process of claim 1 wherein said hydrocarbons are preheated to a temperature not greater than about 400° F.

3. The process of claim 1 wherein said reaction product is diluted with a quenching gas.

4. The process of claim 3 wherein said quenching gas is water vapor.

5. The process of claim 3 wherein said quenching gas is methane.

6. The process of claim 1 wherein said oxygen-containing gas comprises oxygen.

7. The process of claim 1 wherein said hydrocarbons comprise natural gas.

8. The process of claim 7 wherein said natural gas contains methane.

9. The process of claim 1 wherein said power is at least 80 percent of the theoretical power resulting from said expansion.

10. The process of claim 1 wherein said reaction product comprises at least 2 percent acetylene.

11. The process of claim 1 wherein said steps are repeated from about 800 to about 1400 times per minute.

12. The process of claim 11 wherein said steps are about 1000 to about 1200 times per minute.

13. The process of claim 1 wherein said mole ratio is from about 1.2:1 to about 1.3:1.

14. The process of claim 1 wherein said oxygen-containing gas comprises a stoichiometric amount necessary for combustion of said portion of said compressed hydrocarbons.

15. The process of claim 2 wherein said portion of compressed hydrocarbons comprise about 20 percent of said introduced hydrocarbons.

16. The process of claim 1 wherein said oxygen-containing gas comprises additionally hydrogen.

17. The process of claim 1 wherein said oxygen-containing gas is introduced to a second reaction zone in fluid communication with said first reaction zone.

18. The process of claim 16 wherein said oxygen-containing gas comprises a mole ratio of hydrogen to oxygen of from about 1.95:1 to about 2.2:1.

19. The process of claim 18 wherein said oxygen-containing gas comprises a mole ratio of about 2.05:1.

* * * * *